(12) United States Patent
Epoune Lingome et al.

(10) Patent No.: US 9,969,762 B2
(45) Date of Patent: May 15, 2018

(54) METHOD FOR SYNTHESIZING N-ALKYL-GLYCOSYL(DI)AMINE DERIVATIVES AND USES OF SAME AGAINST PHYTOPATHOGENS

(71) Applicants: SIPRE, Achicourt (FR); Universite de Picardie Jules Verne, Amienes (FR)

(72) Inventors: Cédric Epoune Lingome, Amiens (FR); Anne Wadouachi, Rivery (FR); Gwladys Pourceau, Louplande (FR); Amélie Beury, Beaurains (FR); Virginie Gobert-Deveaux, Thumesni (FR)

(73) Assignees: SIPRE, Achicort (FR); Universite De Picardie Jules Verne, Amiens Cedex (FR)

( * ) Notice: Subject to any disclaimer, the term of this patent is extended or adjusted under 35 U.S.C. 154(b) by 0 days. days.

(21) Appl. No.: 14/894,297

(22) PCT Filed: May 28, 2014

(86) PCT No.: PCT/IB2014/061779
§ 371 (c)(1),
(2) Date: Nov. 25, 2015

(87) PCT Pub. No.: WO2014/195828
PCT Pub. Date: Dec. 11, 2014

(65) Prior Publication Data
US 2016/0102115 A1    Apr. 14, 2016

(30) Foreign Application Priority Data
May 31, 2013    (FR) ...................................... 13 55024

(51) Int. Cl.
| C07H 15/12 | (2006.01) |
| A01N 43/16 | (2006.01) |
| C07H 15/26 | (2006.01) |
| A01N 33/08 | (2006.01) |
| A01N 33/12 | (2006.01) |

(52) U.S. Cl.
CPC ............. *C07H 15/12* (2013.01); *A01N 33/08* (2013.01); *A01N 33/12* (2013.01); *A01N 43/16* (2013.01); *C07H 15/26* (2013.01)

(58) Field of Classification Search
CPC ........ C07H 15/12; C07H 15/26; A01N 43/16; A01N 33/08; A01N 33/12
USPC ............................ 514/53, 42; 536/17.2, 29.1
See application file for complete search history.

(56) References Cited

U.S. PATENT DOCUMENTS

| 4,638,816 A * | 1/1987 | Cox ........................ C07H 5/06 |
| | | 131/276 |
| 5,786,468 A * | 7/1998 | Au ........................ C11D 1/528 |
| | | 510/470 |

FOREIGN PATENT DOCUMENTS

WO    01/05224 A1    1/2001

OTHER PUBLICATIONS

Mitts et al. The Reaction of Glucose with Some Amines. J Am Chem Soc 66:483-486, 1944.*
Thorwirth et al. Switchable Selectivity during Oxidation of Anilines in a Ball Mill. Chem. Eur. J. 16:13236-13242, 2010.*
Chupakhina, T.A., et al., "Synthesis and Investigation of Antimicrobial Activity of 8-Hydroxyquinoline Glucosaminides," Russian Journal of Bioorganic Chemistry 38(4):422-427, Jul. 2012.
Iddon, L., et al., "Systheses and Structures of Anomeric Quaternary Ammonium β-Glucosides and Comments on the Anomeric C—N Bond Lengths," Tetrahedron 65(32):6396-6402, Aug. 2009.
International Search Report dated Sep. 15, 2014, issued in corresponding International Application No. PCT/IB2014/061779, filed May 28, 2014, 10 pages.
Mack, J., and S. Muthukrishnan, "Solvent-Free Synthesis," in W. Zhang and B.W. Cue, Jr. (eds.), Green Techniques for Organic Synthesis and Medicinal Chemistry, John Wiley & Sons Ltd., Chichester, U.K., Jun. 2012, Chapter 11.
Muhizi, T., et al., "Synthesis and Evaluation of N-Alkyl-β-D-Glucosylamines on the Growth of Two Wood Fungi, Coriolus versicolor and Poria placenta," Carbohydrate Research 343(14):2369-2375, Sep. 2008.
Muhizi, T., et al., "Synthesis of N-Alkyl-β-D-Glucosylamines and Their Antimicrobial Activity against Fusarium proliferatum, Salmonella typimurium, and Listeria innocua," Journal of Agricultural and Food Chemistry 57 (23):11092-11099, Dec. 2009.
Neto, V., et al., "Influence of the Variation of the Alkyl Chain Length of N-Alkyl-β-D-Glucosylamine Derivatives on Antifungal Properties," Journal of Agricultural and Food Chemistry 60(42):10375-10714, Oct. 2012.
Ricco-Lattes, I., and A. Lattes, "Synthesis of New Sugar-Based Surfactants Having Biological Applications: Key Role of Their Self-Association," Colloids and Surfaces A: Physicochemical and Engineering Aspects 123-124:37-48, May 1997.

* cited by examiner

*Primary Examiner* — Yih-Horng Shiao
(74) *Attorney, Agent, or Firm* — Christensen O'Connor Johnson Kindness PLLC

(57) ABSTRACT

The present invention relates to a novel method for synthesizing, without a solvent, N-alkyl-glycosyl(di)amine derivatives represented by the following general formula (I): The invention also concerns the use of N-alkyl-glycosyl(di) amine derivatives represented by the general formula (I), and N-alkyl-glycosyl(di)ammonium quaternary salts represented by the general formula (II) and N-alkyl-glycamine derivatives represented by the general formula (III) obtained from N-alkyl-glycosyl(di)amine derivatives represented by the general formula (I), as antibacterial and/or antifungal agents against phytopathogens.

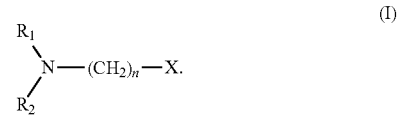

16 Claims, 1 Drawing Sheet

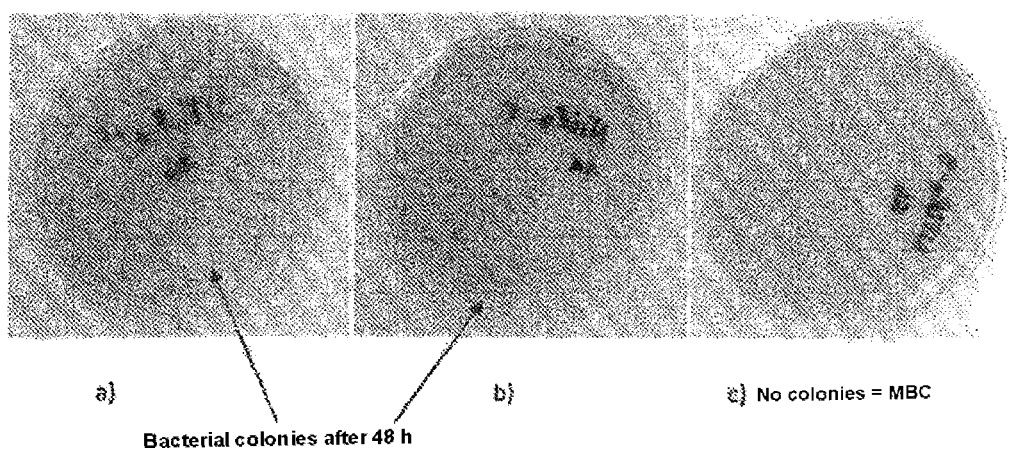

METHOD FOR SYNTHESIZING N-ALKYL-GLYCOSYL(DI)AMINE DERIVATIVES AND USES OF SAME AGAINST PHYTOPATHOGENS

The subject of the present invention is a novel process for the solvent-free synthesis of N-alkyl-glycosyl(di)amine derivatives corresponding to general formula (I) below:

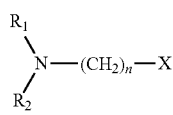

The invention also relates to the use of N-alkyl-glycosyl (di)amine derivatives corresponding to general formula (I), as antibacterial and/or antifungal agents against phytopathogens. Finally, the invention relates to the use of quaternary N-alkyl-glycosyl(di)ammonium salts corresponding to general formula (II) and of N-alkyl-glycamine derivatives corresponding to general formula (III), obtained from N-alkyl-glycosyl(di)amine derivatives corresponding to general formula (I), as antibacterial and/or antifungal agents against phytopathogens.

For several years, the synthesis of bioactive molecules with a wide spectrum of action (antibacterials, antifungals, antivirals, nematicides, natural-defense elicitors), capable of inhibiting and/or eradicating phytopathogens of plants such as potato, tomato, grapevine or beetroot, has experienced a growing interest. Indeed, the synthesis of such molecules is an economic and environmental challenge of the first order, these molecules having a very high added value and a low ecotoxicity, while at the same time meeting the requirements of biocompatibility and biodegradability. The chemistry implemented for the synthesis of these molecules must therefore be sustainable chemistry, governed by principles such as economy of atoms, the design of chemical products that are less harmful and safer, the use of safer solvents and auxiliary products, the improvement of energy yields, the use of renewable raw materials such as carbohydrates (sugars), the reduction of the amount of derived products, or catalysis.

The present invention is along these lines. It relates to a novel process, termed "green chemistry process", for the synthesis of N-alkyl-glycosyl(di)amine derivatives used as biocides against phytopathogens. Processes for the preparation of N-(dialkylamino)alkyl-glycosylamine derivatives have in fact already been described in the prior art (applications FR 2 767 134, FR 2 661 413 and FR 2 440 159). However, these syntheses have always been carried out in a solvent medium.

The N-alkyl-glycosyl(di)amine derivatives obtained according to the process of the invention are "biobased" compounds, potentially less toxic than the pesticides normally used, and capable of combating the phytopathogens present in soils, such as Gram-negative bacteria responsible for example for crown gall caused by the pathogenic agent *Agrobacterium tumefaciens*, or for blackleg in potato, caused by bacteria of the *Pectobacterium* and *Dickeya* genera. Indeed, there is no means for chemically combating blackleg disease which affects potato fields, and also the tubers during storage, only prophylactic methods which look after limiting the dissemination thereof are used at the current time.

The inventors have therefore given themselves the objective of designing a process for the synthesis of N-alkyl-glycosyl(di)amine derivatives by mechanosynthesis, which is safer than the processes normally used since it does not use harmful organic solvent, said process resulting in very good yields. Mechanosynthesis processes, previously intended for the preparation of inorganic compounds, can therefore today be adapted to the synthesis of glycosylated compounds.

Thus, the first subject of the invention relates to a process for the solvent-free synthesis of N-alkyl-glycosyl(di)amine derivatives corresponding to general formula (I) below:

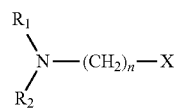

in which:
- $R_1$ is a glycosyl radical, and preferably a mono-, oligo- or polysaccharide residue,
- $R_2$ represents a hydrogen atom, a glycosyl radical, or a $C_1$-$C_{22}$ alkyl radical,
- n is an integer ranging from 0 to 22,
- X represents a halogen atom, an alkyl, alkenyl or alkynyl radical, a hydroxyl group, a carboxyl or carbaldehyde group, an aryl or heteroaryl group, or an —$NR_3R_4$ group, in which $R_3$ represents a hydrogen atom or a glycosyl radical, and preferably a mono-, oligo- or polysaccharide residue, and $R_4$ represents a hydrogen atom or a $C_1$-$C_{12}$ alkyl radical, with the proviso that n is different from 0 when X is an —$NR_3R_4$ group, said process comprising the following steps:
(i) mixing an ose or oside compound and an amine of formula $R_2NH$—$(CH_2)_n$—X in a reactor, preferably in a vibratory mill or in a reactor for ball-milling which is vibrational or planetary, and
(ii) milling said mixture in a ball mill.

For the purposes of the present invention:
- The term "alkyl" is intended to mean: a linear or branched, saturated hydrocarbon-based aliphatic group which can contain from 1 to 22 carbon atoms, preferably 1 to 12 carbon atoms, and even more preferentially 1 to 6 carbon atoms. The term "branched" signifies that at least one lower alkyl group such as a methyl or an ethyl is borne by a linear alkyl chain. By way of alkyl group, mention may be made of, for example, methyl, ethyl, n-propyl, i-propyl, n-butyl, t-butyl, n-pentyl, n-hexyl, n-heptyl, n-octyl, n-nonyl, n-decyl, n-undecyl and n-dodecyl groups;
- The term "alkenyl" is intended to mean: a linear or branched, hydrocarbon-based aliphatic group which has an unsaturation characterized by the presence of a carbon-carbon double bond. The alkene preferably contains 2 to 12 carbon atoms, and even more preferentially 2 to 6 carbon atoms;
- The term "alkynyl" is intended to mean: a linear or branched, hydrocarbon-based aliphatic group which has an unsaturation characterized by the presence of a carbon-carbon triple bond. The alkyne preferably contains 2 to 12 carbon atoms, and even more preferentially 2 to 6 carbon atoms;

The term "aryl" is intended to mean: any functional or substituent group derived from at least one aromatic ring; an aromatic ring corresponds to any planar mono- or polycyclic group comprising a delocalized π system in which each atom of the ring comprises an orbital p, said orbitals p overlapping one another; among such aryl groups, mention may be made of phenyl, biphenyl, naphthalene and anthracene groups. The aryl groups of the invention preferably comprise from 6 to 22 carbon atoms, preferably from 6 to 12 carbon atoms, and even more preferably 5 or 6 carbon atoms;

The term "heteroaryl" is intended to mean: any functional or substituent group derived from at least one aromatic ring as defined above and containing at least one heteroatom chosen from P, S, O and N; among the heteroaryl groups, mention may be made of furan, pyridine, pyrrole, thiophene, imidazole, pyrazole, oxazole, isoxazole, triazole, triazole, tetrazole, pyridine, pyrazine, pyrimidine, pyridazine, benzofuran, isobenzofuran, indole, isoindole, benzothiophene, benzo[c]thiophene, benzimidazole, indazole, benzoxazole, benzisoxazole, benzothiazole, quinoline, isoquinoline, quinoxaline, quinazoline, cinnoline, purine and acridine. The aryl groups of the invention preferably comprise from 4 to 22 carbon atoms, preferably from 4 to 12 carbon atoms, and even more preferably 5 or 6 carbon atoms;

The halogen atoms are chosen from bromine, chlorine, fluorine and iodine atoms, and preferably from bromine, chlorine and iodine atoms.

The ose or oside compound of the invention is a mono-, oligo- or polysaccharide which can comprise from 1 to 20 monosaccharide units. The term "ose compound" is intended to mean any reducing sugar capable of reacting with a nucleophilic amine. The term "oside compound" is intended to mean any sugar comprising an electrophilic site in a position other than the anomeric position, capable of reacting with a nucleophilic amine. Advantageously, the saccharide unit is chosen from threose, erythrose, deoxyribose, ribose, xylose, rhamnose, fucose, glycerose, arabinose, lyxose, allose, altrose, gulose, idose, talose, glucose, mannose, glucosamine, galactosamine, maltose, lactose and galactose, and preferably from rhamnose, glucose, maltose, lactose or galactose, and even more preferably from rhamnose, glucose or galactose.

The process of the invention may comprise a prior step during which the amine of formula $R_2NH—(CH_2)_n—X$ is mixed with an auxiliary, preferably by means of a mortar, it being possible for said auxiliary to be neutral or basic and chosen from silica ($SiO_2$), alumina ($Al_2O_3$), clays and carbonates. This prior step of mixing with an auxiliary quantitatively improves the yield of the synthesis, the inventors having observed an improvement in the yields from 40-60% to 75-97% when the amine is premixed with an auxiliary.

The term "auxiliary" is intended to mean an agent which allows a better dispersion of powders. It may or may not be chemically inert, and is chosen from silica, alumina, clays such as the montmorillonite clays K10 or KSF, and carbonates such as sodium carbonate or potassium carbonate.

During step (i), the mole ratio of the ose or oside compound to the amine may be between 1/1 and 1/1.2.

The milling step (ii) may last at least 1 hour, and preferably from 1 to 4 hours. During this step (ii), the mill preferably operates at a frequency of between 20 and 50 Hz, and preferably at 50 Hz.

According to one preferred embodiment, the reactor and/or the balls of the mill are made of stainless steel, of tungsten carbide or of zirconia. The reactor and the balls of the mill preferably consist of the same material.

According to one particularly preferred embodiment, the balls of the mill and the mixture of the ose or oside compound and of the amine of formula $R_2NH—(CH_2)_n—X$ represent at least ⅓ of the reactor volume.

The process of the invention may also comprise an additional purification and/or filtration step (iii). When the process of the invention is carried out without a prior impregnation step, step (iii) is preferably a step of purification on silica. When the process of the invention is carried out with a prior impregnation step, step (iii) is preferably a step of filtration on silica, on a column or on a sinter.

According to a first alternative, the process of the invention may comprise a subsequent step (iv) of converting the N-alkyl-glycosyl(di)amine derivative of formula (I) into a quaternary N-alkyl-glycosyl(di)ammonium salt by reaction with a quaternizing agent of formula $R_5—Y$, in which:

$R_5$ represents a hydrogen atom or a $C_1$-$C_{22}$ alkyl radical, and

Y represents a halogen atom, a sulfate group $R_6O—SO_2—O—$ or a sulfonate group $R_6—SO_2—O—$, in which $R_6$ is a $C_1$-$C_{12}$ alkyl radical, it being possible for the sulfonate groups to be triflate, tosylate, mesylate or nosylate groups.

According to one preferred embodiment, the quaternary N-alkyl-glycosyl(di)ammonium salt of step (iv) is obtained after reaction of the N-alkyl-glycosyl(di)amine derivative with an excess of quaternizing agent in a vibratory mill or in a reactor for ball-milling which is vibrational or planetary.

The quaternary N-alkyl-glycosyl(di)ammonium salt obtained corresponds to formula (II) below:

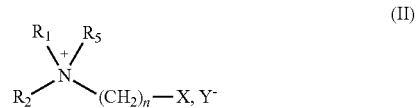

(II)

in which $R_1$, $R_2$, n and X are as defined previously, and:

$R_5$ represents a hydrogen atom or a $C_1$-$C_{22}$ alkyl radical, and

Y represents a halide ion, a sulfate ion $R_6O—SO_2—O^-$ or a sulfonate ion $R_6—SO_2—O^-$, in which $R_6$ is a $C_1$-$C_{12}$ alkyl radical, it being possible for the sulfonate ions to be triflate, tosylate, mesylate or nosylate ions, on the condition that n is other than 0 when X is an $—NR_3R_4$ group.

The excess of quaternizing agent may be between 1.5 and 10 molar equivalents relative to the N-alkyl-glycosyl(di)amine derivative of formula (I), and preferably between 2.5 and 5 molar equivalents.

During step (iv), the milling may last at least 2 h, and preferably 7 h.

The purification of the quaternary N-alkyl-glycosyl(di)ammonium salt of formula (II) may be carried out according to a process comprising an acetylation step, followed by an evaporation step and a settling-out step with an organic solvent and distilled water. During the acetylation step, the $Y^-$ ion can be converted into a carboxylate ion $R_6—COO^-$, in which $R_6$ is a $C_1$-$C_{12}$ alkyl radical. Finally, a step of lyophilization or drying of the aqueous phase, and a step of filtration of silica gel, can be carried out in order to isolate the quaternary N-alkyl-glycosyl(di)ammonium salt of formula (II).

Preferably, the purification of the quaternary N-alkyl-glycosyl(di)ammonium salt of formula (II) is carried out according to a process comprising an acetylation step using a mixture of acetic anhydride with an acid compound or a mixture of acetic anhydride with a basic compound or a mixture of acetyl chloride with a basic compound. The preferred mixture used for the acetylation is a mixture of acetic anhydride and cerium triflate.

According to a second alternative, the process of the invention may comprise a subsequent step (iv') of converting the N-alkyl-glycosyl(di)amine derivative of formula (I) into an N-alkyl-glycamine derivative by milling the N-alkyl-glycosyl(di)amine derivative of formula (I) with a reducing agent and an acid, in the presence of a polar solvent.

The N-alkyl-glycamine derivative obtained corresponds to formula (III) below:

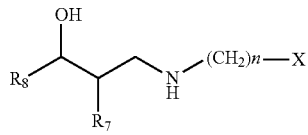

(III)

in which n and X are as defined previously, and:
  $R_7$ represents a hydrogen atom or an —OH or —NH$_2$ group, and
  $R_8$ represents a hydrogen atom or a —CH(OR$_9$)R$_{10}$ group in which $R_9$ represents a hydrogen atom or a glycosyl radical, and preferably a mono-, oligo- or polysaccharide residue, and $R_{10}$ represents a hydrogen atom, or a —CH$_2$OH or —CH(OH)R$_{11}$ group in which $R_{11}$ represents a —CH$_2$OH group or a $C_1$-$C_4$ alkyl radical, and preferably a methyl group.

The milling step (iv') is preferably carried out in a reactor, and even more preferentially in a vibratory mill or in a reactor for ball-milling which is vibrational or planetary.

The reducing agent is advantageously chosen from metal borohydrides such as NaBH$_4$, LiBH$_4$, NaBH$_3$CN, LiBH$_3$CN, NaBH(OAc)$_3$, LiBH(OAc)$_3$, ZnBH$_4$, L-selectride of formula $C_{12}H_{27}BLi$, diborane B$_2$H$_6$, or an aluminum hydride chosen from LiAlH$_4$, LiAlH(O-tBu)$_3$, diisobutylaluminum hydride (or DIBAL) of formula $C_8H_{19}Al$, sodium bis(2-methoxyethoxy)aluminum hydride (or Red-Al) of formula $C_6H_{16}AlNaO_4$, or covalent hydrides such as GaH$_3$ or NaGaBH$_4$. The preferred reducing agent is NaBH$_4$.

For the purposes of the present invention, the term "acid" is intended to mean a Lewis acid or a Brönsted acid, preferably a Brönsted acid bearing a carboxylic or sulfonic acid function. Advantageously, the acid used is para-toluenesulfonic acid or benzoic acid.

The milling is preferably carried out in the presence of a catalytic amount of polar solvent. The percentage by weight of polar solvent relative to the total weight of the reagents can vary from 10% to 50% by weight, and preferably between 10% and 20% by weight. The polar solvent may be chosen from dimethyl sulfoxide (DMSO), dimethylformamide (DMF), acetonitrile, ethanol, methanol, butanol, propanol, isopropanol, water and acetone, the preferred polar solvents being methanol and ethanol.

According to one advantageous embodiment, the milling step (iv') may comprise a prior milling of the N-alkyl-glycosyl(di)amine derivative of formula (I) with the reducing agent and the acid, followed by the addition of the polar solvent, and then a further milling step, this time in the presence of the polar solvent. The prior milling may last from 1 to 30 minutes, preferably from 5 to 15 minutes, and even more preferentially 10 minutes. The milling in the presence of the polar solvent may last from 5 to 30 minutes, preferably from 10 to 20 minutes, and even more preferentially 15 minutes.

The purification of the N-alkyl-glycamine deriviate of formula (III) can be carried out according to a process comprising a quaternization step, followed by a filtration step and by a step of regeneration of the amine on an ion exchange resin in an organic solvent. Finally, a filtration step, followed by an evaporation step, can be carried out in order to isolate the N-alkyl-glycamine derivative of formula (III).

The quaternization step is preferably carried out in an organic solvent with an acid such as HCl, HBr, H$_3$PO$_4$, H$_2$SO$_4$ or HNO$_3$, and preferably with HCl.

The step of regeneration of the amine is preferably carried out on an anion exchange resin chosen from anionic resins bearing tertiary or quaternary amine groups, and preferably on an Amberlite IRA 402-Cl$^-$ anion exchange resin.

The invention also relates to the use of N-alkyl-glycosyl(di)amine derivatives corresponding to general formula (I) below:

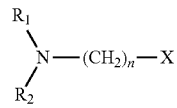

(I)

in which:
  $R_1$ is a glycosyl radical, preferably a mono-, oligo- or polysaccharide residue,
  $R_2$ represents a hydrogen atom, a glycosyl radical, or a $C_1$-$C_{22}$ alkyl radical,
  n is an integer ranging from 0 to 22,
  X represents a halogen atom, an alkyl, alkenyl or alkynyl radical, a hydroxyl group, a carboxyl or carbaldehyde group, an aryl or heteroaryl group, or an —NR$_3$R$_4$ group, in which $R_3$ represents a hydrogen atom or a glycosyl radical, preferably a mono-, oligo- or polysaccharide residue, and $R_4$ represents a hydrogen atom or a $C_1$-$C_{12}$ alkyl radical,
with the proviso that n is different from 0 when X is an —NR$_3$R$_4$ group,
as antibacterial and/or antifungal agents against the following phytopathogens: *Agrobacterium tumefaciens, Pectobacterium atrosepticum, Dickeys dianthicola, Fusarium sambucinum, Fusarium roseum* and *Phytophthora infestans*, the phytopathogens *Pectobacterium atrosepticum, Dickeys dianthicola, Fusarium sambucinum, Fusarium roseum* and *Phytophthora infestans* being potato phytopathogens.

The invention also relates to the use of quaternary N-alkyl-glycosyl(di)ammonium salts corresponding to general formula (II) below:

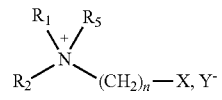

(II)

in which $R_1$, $R_2$, n and X are as defined previously, and:
  $R_5$ represents a hydrogen atom or a $C_1$-$C_{22}$ alkyl radical, and Y represents a halide ion, a sulfate ion $R_6O$—$SO_2$—$O^-$ or a sulfonate ion $R_6$—$SO_2$—$O^-$, in which $R_6$ is a $C_1$-$C_{12}$ alkyl radical, it being possible for the sulfonate ions to be triflate, tosylate, mesylate or nosylate ions, with the proviso that n is different from 0 when X is an —$NR_3R_4$ group, as antibacterial and/or antifungal agents against phytopathogens, in particular against phytopathogens such as: *Agrobacterium tumefaciens, Pectobacterium atrosepticum, Dickeya dianthicola, Fusarium sambucinum, Fusarium roseum* and *Phytophthora infestans*, the phytopathogens *Pectobacterium atrosepticum, Dickeya dianthicola, Fusarium sambucinum, Fusarium roseum* and *Phytophthora infestans* being potato phytopathogens.

Finally, the invention relates to the use of N-alkyl-glycamine derivatives corresponding to general formula (III) below:

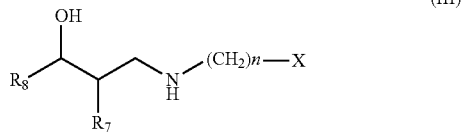

in which n and X are as defined previously, and:
  $R_7$ represents a hydrogen atom or an —OH or —$NH_2$ group, and
  $R_8$ represents a hydrogen atom or a —$CH(OR_9)R_{10}$ group in which $R_9$ represents a hydrogen atom or a glycosyl radical, and preferably a mono-, oligo- or polysaccharide residue, and $R_{10}$ represents a hydrogen atom, or a —$CH_2OH$ or —$CH(OH)R_{11}$ group in which $R_{11}$ represents a —$CH_2OH$ group or a $C_1$-$C_4$ alkyl radical, preferably a methyl group, as antibacterial and/or antifungal agents against the following phytopathogens: *Agrobacterium tumefaciens, Pectobacterium atrosepticum, Dickeya dianthicola, Fusarium sambucinum, Fusarium roseum* and *Phytophthora infestans*, the phytopathogens *Pectobacterium atrosepticum, Dickeya dianthicola, Fusarium sambucinum, Fusarium roseum* and *Phytophthora infestans* being potato phytopathogens.

In addition to the above arrangements, the invention also comprises other arrangements which will emerge from the further description which follows, which refers to examples of implementation of the process of the invention for the synthesis of N-alkyl-glycosyl(di)amine derivatives corresponding to general formula (I), of quaternary N-alkyl-glycosyl(di)ammonium salts corresponding to general formula (II), and of N-alkyl-glycamine derivatives corresponding to general formula (III), and also to the appended FIG. 1 which illustrates the antibacterial activity of N-alkyl-glycosylamine derivatives of formula (I) and of N-alkyl-glycamine derivatives of formula (III) against *Pectobacterium atrosepticum, Agrobacterium tumefaciens* and *Dickeya dianthicola*.

Materials and Methods

Characterization:

The products described in the examples hereinafter were characterized by thin-layer chromatography on Merck glass or aluminum plates coated with a gel of silica 60 $F_{254}$, 0.25 mm thick, for the direct phase. The visualization was carried out by spraying a solution of ninhydrin or of cerium molybdate, followed by heating the plate.

The column chromatography purifications were carried out in the liquid phase on an open column. The stationary phase used is Merck silica gel 60 (70-230 mesh ASTM) (0.063-0.200 µm).

The proton ($^1H$) and carbon ($^{13}C$) NMR spectra were performed on Bruker Advance 300 spectrometers. The chemical shift (δ) values are expressed in parts per million (ppm). The coupling constants J are expressed in Hertz (Hz). The multiplicity of the signals is indicated using the following abbreviations:

s=singlet d=doublet dd=double doublet t=triplet m=multiplet.

The mass spectra were performed on a positive-polarity Q-Tof tandem mass spectrometer. The samples are ionized by electrospray with RID detection. Other spectra were performed on a Waters ZQ spectrometer also in electrospray mode. The compounds were dissolved beforehand in methanol.

EXAMPLE 1: PREPARATION OF A COMPOUND Ia OF FORMULA

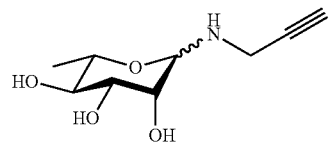

Propargylamine (0.71 g; 2.5 mmol) is mixed with 3 g of neutral alumina ($Al_2O_3$). The reagents are ground in a mortar using a pestle for 2 minutes, then 2.21 g of L-rhamnose monohydrate (12.2 mmol) are added to the mortar. The mixture thus formed is ground using a pestle for 2 minutes, then placed in a stainless steel jar equipped with 4 stainless steel balls which are 13 mm in diameter. The jar is placed in a Spex 8000M vibrational ball mill and agitated for 1 h 30.

The reaction crude is dissolved at reflux in 200 ml of ethanol, then filtered on a sinter comprising 50 g of silica and washed with 100 ml of hot ethanol. After evaporation of the ethanol under reduced pressure, a yellow solid is obtained.

Washing with 10 ml of diethyl ether at 40° C. makes it possible to obtain 2.3 g (94%) of a compound Ia in the form of a pale yellow powder.

Mixture of α,β isomers: α/β: 88/12;

α isomer: $^1H$ NMR ($CD_3OD$): δ 4.18 (d, 1H, J=1.1 Hz, H-1); 3.79 (dd, 1H, J=3.4, 1.0 Hz, H-2); 3.61 (dd, 1H, J=16.4, 2.6 Hz, —HN—$CH_2$—); 3.52 (dd, 1H, J=16.4, 2.6 Hz, —HN—$CH_2$—); 3.42 (dd, 1H, J=9.2, 3.3 Hz, H-3); 3.29 (t, 1H, J=9.2 Hz, H-4); 3.18 (dq, 1H J=9.2, 6.0 Hz, H-5); 2.57 (t, 1H, J=2.5 Hz, HC≡C—); 1.28 (d, 3H, J=6.1 Hz, H-6).

$^{13}C$ NMR ($CD_3OD$): δ 86.7 (C-1), 82.1 (HC≡C—); 75.8 (C-3), 74.6 (C-5), 74.0 (C-4), 72.8 (C-2+HC≡C—), 34.6 (—HN—$CH_2$—), 18.1 (C-6).

High-resolution mass spectrometry HRMS $[M+H]^+$ calculated for $C_9H_{15}NO_4$: m/z 202.1035 found m/z 202.1070.

EXAMPLE 2: PREPARATION OF A COMPOUND Ib OF FORMULA

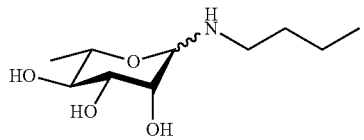

Butylamine (0.45 g; 6.1 mmol) is mixed with 1.5 g of silica (SiO$_2$). The reagents are ground in a mortar using a pestle for 2 minutes, then 1 g of L-rhamnose monohydrate (5.5 mmol) is added to the mortar. The mixture thus formed is ground using a pestle for 2 minutes, then placed in a stainless steel jar equipped with 4 stainless steel balls which are 13 mm in diameter. The jar is placed in a Spex 8000M vibrational ball mill and agitated for 1 h 30.

The reaction crude is dissolved at reflux in 100 ml of ethanol, then filtered on a sinter comprising 50 g of silica and washed with 50 ml of hot ethanol. After evaporation of the ethanol under reduced pressure, an off-white solid is obtained.

Washing with 10 ml of diethyl ether at 40° C., followed by filtration on a sinter, makes it possible to obtain 1.15 g (86%) of a compound Ib in the form of a white powder.

Mixture of α,β isomers: α/β: 94/6;

α isomer: $^1$H NMR (CD$_3$OD): δ4.04 (d, 1H, J=1.1 Hz, H-1); 3.78 (dd, 1H, J=3.3, 1.1 Hz, H-2); 3.40 (dd, 1H, J=9.2, 3.3 Hz, H-3); 3.28 (t, 1H, J=9.2 Hz, H-4); 3.17 (dq, J=9.1, 6.0 Hz, 1H, H-5); 2.93 (ddd, 1H, J=11.6, 8.3, 6.5 Hz, —HN—CH$_2$—); 2.59 (ddd, 1H, J=11.6, 8.4, 5.9 Hz, —HN—CH$_2$—); 1.58-1.30 (m, 4H, —CH$_2$—CH$_2$—); 1.27 (d, 3H, J=6.0 Hz, H-6); 0.94 (t, 3H J=7.2 Hz, CH$_3$—CH$_2$).

$^{13}$C NMR (CD$_3$OD): δ 88.4 (C-1), 76.0 (C-3), 74.7 (C-5), 74.1 (C-4), 73.1 (C-2), 46.0 (—HN—C$_2$—), 33.2 (—HN—CH$_2$—CH$_2$—), 21.5 (—CH$_2$—CH$_3$), 18.1 (C-6), 14.3 (CH$_3$—CH$_2$).

High-resolution mass spectrometry HRMS [M+H]$^+$ calculated for C$_{10}$H$_{21}$NO$_4$: m/z 220.1549 found m/z 220.1546.

EXAMPLE 3: PREPARATION OF A COMPOUND Ic OF FORMULA

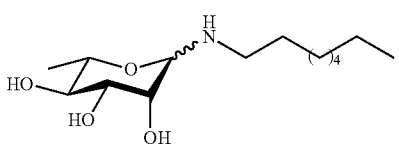

Octylamine (0.79 g; 6.1 mmol) is mixed with 1.5 g of silica (SiO$_2$). The reagents are mixed and ground in a mortar using a pestle for 2 minutes, then 1 g of L-rhamnose monohydrate (5.5 mmol) is added to the mortar. The mixture thus formed is ground using a pestle for a further 2 minutes, then placed in a stainless steel jar equipped with 4 stainless steel balls which are 13 mm in diameter. The jar is placed in a Spex 8000M vibrational ball mill and agitated for 1 h 30.

The reaction crude is dissolved at reflux in 100 ml of ethanol, then filtered on a sinter comprising 50 g of silica and washed with 50 ml of hot ethanol. After evaporation of the ethanol under reduced pressure, an off-white solid is obtained.

Washing with 10 ml of diethyl ether at 40° C., followed by filtration on a sinter, makes it possible to obtain 1.29 g (85%) of a compound Ic in the form of a white powder.

Mixture of α,β isomers: α/β: 93/7;

α isomer: $^1$H NMR (CD$_3$OD): δ 4.04 (d, 1H, J=1.1 Hz, H-1); 3.78 (dd, 1H, J=3.3, 1.1 Hz, H-2); 3.40 (dd, 1H, J=9.2, 3.3 Hz, H-3); 3.28 (t, 1H, J=9.2 Hz, H-4); 3.18 (dq, 1H, J=9.2, 6.0 Hz, H-5); 2.91 (ddd, 1H, J=11.6, 8.4, 6.4 Hz, —HN—CH$_2$—); 2.59 (ddd, 1H, J=11.6, 8.4, 5.9 Hz, —HN—CH$_2$—); 1.61-1.41 (m, 2H, —NH$_2$—CH$_2$—CH$_2$—); 1.40-1.29 (m, 10H, —CH$_2$—CH$_2$—); 1.28 (d, 3H, J=5.9 Hz, H-6); 0.90 (t, 3H J=6.8 Hz, CH$_3$—CH$_2$—).

$^{13}$C NMR (CD$_3$OD): δ 88.4 (C-1), 76.0 (C-3), 74.6 (C-5), 74.1 (C-4), 73.1 (C-2), 46.3 (—HN—CH$_2$—), 33.0, 31.0, 30.6, 30.4, 28.4, 23.7 (—CH$_2$—CH$_2$—), 18.1 (C-6), 14.4 (CH$_3$—CH$_2$—).

High-resolution mass spectrometry HRMS [M+H]$^+$ calculated for C$_{14}$H$_{29}$NO$_4$: m/z 276.2175 found m/z 276.2182.

EXAMPLE 4: PREPARATION OF A COMPOUND Id OF FORMULA

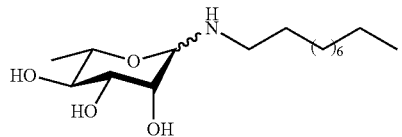

Decylamine (1 g; 6.6 mmol) is mixed with 1.5 g of silica (SiO$_2$). The reagents are then mixed and ground in a mortar using a pestle for 2 minutes, then 1 g of L-rhamnose monohydrate (5.5 mmol) is added to the mortar. The mixture thus formed is ground using a pestle for a further 2 minutes, then placed in a stainless steel jar equipped with 4 stainless steel balls which are 13 mm in diameter. The jar is placed in a Spex 8000M vibrational ball mill and agitated for 1 h 30.

The reaction crude is dissolved at reflux in 100 ml of ethanol, then filtered on a sinter comprising 50 g of silica and washed with 50 ml of hot ethanol. After evaporation of the ethanol under reduced pressure, an off-white solid is obtained.

Washing with 10 ml of diethyl ether at 40° C., followed by filtration on a sinter, makes it possible to obtain 1.58 g (95%) of a compound Id in the form of a white powder.

Mixture of α,β isomers: α/β: 91/9;

α isomer: $^1$H NMR (CD$_3$OD): δ4.04 (d, 1H, J=1.1 Hz, H-1; 3.78 (dd, 1H, J=3.3, 1.1 Hz, H-2); 3.40 (dd, 1H, J=9.2, 3.3 Hz, H-3); 3.28 (t, 1H, J=9.2 Hz, H-4); 3.17 (dq, 1H, J=9.1, 6.0 Hz, H-5); 2.91 (ddd, 1H, J=11.6, 8.5, 6.5 Hz, —HN—CH$_2$—); 2.59 (ddd, 1H, J=11.4, 8.4, 5.9 Hz, —HN—CH$_2$—); 1.61-1.41 (m, 2H, —NH$_2$—CH$_2$—); 1.41-1.29 (m, 6H, —CH$_2$—CH$_2$—); 1.27 (d, 3H, J=5.9 Hz, H-6); 0.91 (t, 3H J=6.8 Hz, (CH$_3$—CH$_2$—).

$^{13}$C NMR (CD$_3$OD): δ 88.4 (C-1), 76.0 (C-3), 74.7 (C-5), 74.2 (C-4), 73.1 (C-2), 46.3 (—HN—CH$_2$—), 32.9, 31.0, 28.1, 23.7 (—CH$_2$—CH$_2$—), 18.1 (C-6), 14.4 (CH$_3$—CH$_2$—).

High-resolution mass spectrometry HRMS [M+H]$^+$ calculated for C$_{12}$H$_{25}$NO$_4$: m/z 248.1862 found m/z 248.1864.

EXAMPLE 5: PREPARATION OF A COMPOUND Ie OF FORMULA

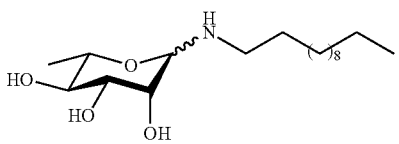

Dodecylamine (1.18 g; 6.3 mmol) is mixed with 1 g of silica ($SiO_2$). The reagents are mixed and ground in a mortar using a pestle for 2 minutes, then 1 g of L-rhamnose monohydrate (5.5 mmol) is added to the mortar. The mixture thus formed is ground using a pestle for a further 2 minutes, then is placed in a stainless steel jar equipped with 4 stainless steel balls which are 13 mm in diameter. The jar is placed in a Spex 8000M vibrational ball mill and agitated for 1 h 30.

The reaction crude is dissolved at reflux in 100 ml of ethanol, then filtered on a sinter comprising 50 g of silica and washed with 50 ml of hot ethanol. After evaporation of the ethanol under reduced pressure, a white solid is obtained.

Washing with 10 ml of diethyl ether at 40° C. makes it possible to obtain 1.53 g (85%) of a compound Ie in the form of a white powder.

Mixture of α,β isomers: α/⊖: 91/9;

α isomer: $^1$H NMR ($CD_3OD$): δ 4.04 (d, 1H, J=0.9 Hz, H-1); 3.78 (dd, 1H, J=3.3, 1.1 Hz, H-2); 3.40 (dd, 1H, J=9.2, 3.3 Hz, H-3); 3.28 (t, 1H, J=9.2 Hz, H-4); 3.17 (dq, 1H, J=9.1, 6.0 Hz, H-5); 2.91 (ddd, 1H, J=11.6, 8.4, 6.5 Hz, —HN—CH$_2$—); 2.59 (ddd, 1H, J=11.6, 8.4, 6.0 Hz, —HN—CH$_2$—); 1.60-1.39 (m, 2H, —HN—CH$_2$—CH$_2$—); 1.39-1.19 (m, 18H, —CH$_2$—CH$_2$—); 1.27 (d, 3H, J=6.1 Hz, H-6); 0.90 (t, 3H J=6.8 Hz, CH$_3$—CH$_2$—).

$^{13}$C NMR ($CD_3OD$): δ 88.4 (C-1), 76.0 (C-3), 74.6 (Cl5), 74.2 (C-4), 73.1 (C-2), 46.3 (—HN—CH$_2$—), 33.0, 31.0, 30.7, 30.6, 30.4, 28.4, 23.7 (—CH$_2$—CH$_2$—), 18.1 (C-6), 14.4 (CH$_3$—CH$_2$).

High-resolution mass spectrometry HRMS [M+H]$^+$ calculated for $C_{18}H_{37}NO_4$: m/z 332.2801 found m/z 332.2816.

EXAMPLE 6: PREPARATION OF A COMPOUND If OF FORMULA

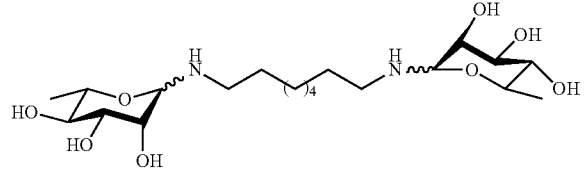

1,8-Diaminooctane (0.5 g; 3.49 mmol) is mixed with 1.26 g of L-rhamnose monohydrate (6.93 mmol) in a mortar using a pestle for 2 minutes, then placed in a stainless steel jar equipped with 4 stainless steel balls which are 13 mm in diameter. The jar is placed in a Spex 8000M vibrational ball mill and agitated for 3 h 20.

The reaction crude is dissolved at reflux in 100 ml of ethanol, then evaporated under reduced pressure to obtain 1.45 g (96%) of a compound If in the form of a white powder.

Mixture of α,α β,β isomers: α/β: 82/18;

α,α isomer: $^1$H NMR (DMSO-d$_6$): δ 4.61 (d, 2H, J=4.9 Hz, OH-4); 4.53 (d, 2H, J=5.0 Hz, OH-2), 4.50 (d, 2H, J=5.7, 5.7, OH-3), 3.89 (s, 2H, H-1) 3.53 (t, 2H, J=3.7 Hz, H-2); 3.23-3.15 (m, 2H, H-3); 3.14-2.93 (m, 4H, H-4, H-5), 2.86-2.72 (m, 2H—HN—CH$_2$—); 2.52-2.38 (m, 2H, —HN—CH$_2$—); 2.08 (s; 2H, —NH—); 1.45-1.30 (m, 4H, —CH$_2$—CH$_2$—NH—), 1.30-1.20 (m, 8H, —CH$_2$—CH$_2$—); 1.12 (d, 6H, J=6.0 Hz, H-6).

$^{13}$C NMR (DMSO-d$_6$): δ87.2 (C-1), 74.4 (C-3), 72.5 (C-5), 72.4 (C-4), 71.6 (C-2), 44.9 (—HN—CH$_2$—$_2$—), 30.0, 29.0, 26.8 (—CH$_2$—CH$_2$—), 18.1 (C-6).

High-resolution mass spectrometry HRMS [M+H]$^+$ calculated for $C_{20}H_{40}N_2O_8$: m/z 437.2866 found m/z 437.2872.

EXAMPLE 7: PREPARATION OF A COMPOUND Ig OF FORMULA

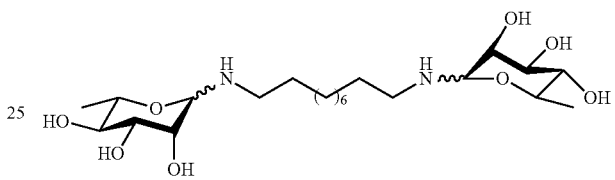

1,10-Diaminodecane (0.5 g; 2.9 mmol) is mixed with 1.06 g of L-rhamnose monohydrate (5.8 mmol) in a mortar using a pestle for 2 minutes, then the mixture is placed in a stainless steel jar equipped with 4 stainless steel balls which are 13 mm in diameter. The jar is placed in a Spex 8000M vibrational ball mill and agitated for 3 h 20.

The reaction crude is dissolved at reflux in 100 ml of ethanol and then evaporated under reduced pressure to give 1.29 g (96%) of the compound If in the form of a white powder.

Mixture of α,α and β,β isomers: α,α/β,β: 84/16;

α,α isomer: $^1$H NMR (DMSO-d$_6$): δ 4.61 (d, 2H, J=4.6 Hz, OH-4); 4.54-4.49 (m, 4H, OH-2 OH-3); 3.88 (s, 2H, H-1), 3.60-3.49 (m, 2H, H-2); 3.18-3.14 (m, 2H, H-3); 3.10-2.93 (m, 4H, H-4, H-5), 2.84-2.70 (m, 2H, —HN—CH$_2$—); 2.51-2.36 (m, 2H, —HN—CH$_2$—); 2.08 (s; 2H, —NH—); 1.42-1.30 (m, 4H, —CH$_2$CH$_2$—NH—), 1.29-1.19 (m, 12H, —CH$_2$—CH$_2$—), 1.12 (d, 6H, J=5.8 Hz, H-6).

$^{13}$C NMR (DMSO-d$_6$): δ87.2 (C-1), 74.4 (C-3), 72.5 (C-5), 72.4 (C-4), 71.6 (C-2), 44.9 (—HN—CH$_2$—), 30.0, 29.0, 26.8 (—CH$_2$—CH$_2$—), 18.1 (C-6).

High-resolution mass spectrometry HRMS [M+H]$^+$ calculated for $C_{22}H_{44}N_2O_8$: m/z 465.3179 found m/z 465.3176.

EXAMPLE 8: PREPARATION OF A COMPOUND Ih OF FORMULA

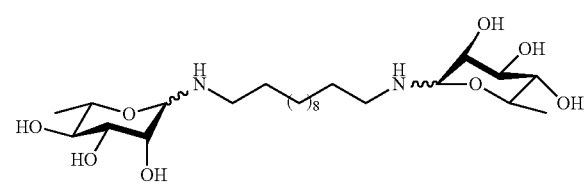

1,12-Diaminododecane (1 g; 5 mmol) is mixed with 1.81 g of L-rhamnose monohydrate (10 mmol) in a mortar using a pestle for 2 minutes. The mixture is placed in a stainless steel jar equipped with 4 stainless steel balls which are 13 mm in diameter. The jar is placed in a Spex 8000M vibrational ball mill and agitated for 3 h 20.

The reaction crude is dissolved at reflux in 100 ml of ethanol, then evaporated under reduced pressure to obtain 2.4 g (98%) of the compound Ih in the form of a white powder.

Mixture of α,α β,β isomers: α,α/β,β: 89/11;

α,α isomer: $^1$H NMR (CD$_3$OD): δ4.04 (d, 2H, J=1.1 Hz, H-1); 3.78 (dd, 2H, J=3.3, 1.1 Hz, H-2); 3.40 (dd, 2H, J=9.2, 3.5 Hz, H-3); 3.28 (t, 2H, J=9.0 Hz, H-4); 3.17 (dq, 2H, J=9.1, 6.0 Hz, H-5); 2.91 (ddd, 2H, J=11.6, 8.4, 6.5 Hz, —HN—CH$_2$—); 2.59 (ddd, 2H, J=11.6, 8.3, 5.9 Hz, —HN—CH$_2$—); 1.60-1.42 (m, 4H, —CH$_2$—CH$_2$—NH—); 1.41-1.29 (m, 16H, —CH$_2$—CH$_2$—); 1.28 (d, 6H, J=5.9 Hz, H-6).

$^{13}$C NMR (CD$_3$OD): δ 88.4 (C-1), 76.0 (C-3), 74.7 (C-5), 74.2 (C-4), 73.1 (C-2), 46.3 (—HN—CH$_2$—), 31.0, 30.7, 30.6, 28.4 (—CH$_2$—CH$_2$—), 18.1 (C-6).

High-resolution mass spectrometry HRMS [M+H]$^+$ calculated for C$_{24}$H$_{48}$N$_2$O$_8$: m/z 493.3513 found m/z 493.3492.

EXAMPLE 9: PREPARATION OF A COMPOUND Ii OF FORMULA

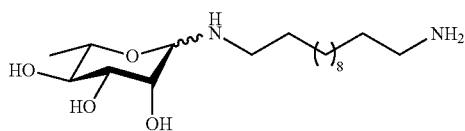

1,12-Diaminododecane (1 g; 5 mmol) is mixed with 0.90 g of L-rhamnose monohydrate (4.9 mmol) in a mortar using a pestle for 2 minutes, then placed in a stainless steel jar equipped with 4 stainless steel balls which are 13 mm in diameter. The jar is placed in a Spex 8000M vibrational ball mill and agitated for 3 h 20.

The crude is purified by silica gel chromatography with a dichloromethane/methanol mixture, the proportions of which gradually vary from 100/0 to 50/50 to obtain 1.31 g (76%) of a compound Ii in the form of a white powder.

Mixture of α, β isomers: α/β: 93/7;

α isomer: $^1$H NMR (CD$_3$OD): δ 4.04 (d, 1H, J=1.1 Hz, H-1); 3.78 (dd, 1H, J=3.3, 0.9 Hz, H-2); 3.40 (dd, 1H, J=9.2, 3.3 Hz, H-3); 3.28 (t, 1H, J=9.2 Hz, H-4); 3.18 (dq, 1H, J=9.2, 5.9 Hz, H-5); 2.91 (ddd, 1H, J=11.6, 8.4, 6.6 Hz, —HN—CH$_2$—); 2.66-2.50 (m, 3H, —NH—CH$_2$—+—CH$_2$—NH$_2$); 1.57-1.40 (m, 4H, —CH$_2$—NH—+—CH_CH$_2$—NH$_2$); 1.40-1.29 (m, 16H, —CH$_2$—CH$_2$—); 1.27 (d, 3H J=5.9 Hz, H-6).

$^{13}$C NMR (CD$_3$OD): δ88.4 (C-1), 76.0 (C-3), 74.7 (C-5), 74.2 (C-4), 73.1 (C-2), 46.3 (—HN—CH$_2$—), 42.5 (—HN—CH$_2$—, 33.7, 31.0, 30.7, 30.6, 28.4, 28.0 (—CH$_2$—CH$_2$—), 18.1 (C-6).

High-resolution mass spectrometry HRMS [M+H]$^+$ calculated for C$_{18}$H$_{38}$N$_2$O$_4$: m/z 347.2910 found m/z 347.2903.

EXAMPLE 10: PREPARATION OF A COMPOUND Ij OF FORMULA

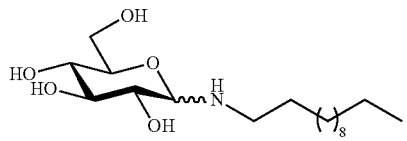

Dodecylamine (1.13 g; 6.2 mmol) is mixed with 1 g of silica (SiO$_2$). The reagents are then mixed and ground in a mortar using a pestle for 2 minutes, then 1 g of glucose (5.5 mmol) is added to the mortar. The mixture thus formed is ground with the pestle for a further 2 minutes, and is then placed in a stainless steel jar equipped with 4 stainless steel balls which are 13 mm in diameter. The jar is placed in a Spex 8000M vibrational ball mill and agitated for 1 h 30.

The reaction crude is dissolved at reflux in 100 ml of ethanol, then filtered on a sinter comprising 50 g of silica and washed with 50 ml of hot ethanol. After evaporation of the ethanol under reduced pressure, a white solid is obtained.

Washing with 10 ml of diethyl ether at 40° C. makes it possible to obtain 1.56 g (81%) of the compound Ij in the form of a white powder.

The $^1$H and $^{13}$C NMR spectra of the compound Ij are in accordance with those described in the literature (Muhizi et al., Carbohydrate Research, 2008, 343, 2369-2375).

Mixture of α,β isomers: the ratio was not accurately determined, however the β isomer is predominant.

β isomer: $^1$H NMR (DMSO-d$_6$): δ 4.81 (d, 1H, J=4.5 Hz, OH-3); 4.77 (d, 1H, J=4.8 Hz, OH-4); 4.42 (d, 1H, J=4.2 Hz, OH-2); 4.32 (t, 1H, J=5.8, OH-6), 3.67-3.61 (m, 2H, H-1+—H-6a); 3.44-3.36 (m, 1H, –H-6b); 3.11 (dt, 1H, J, =8.7, 4.4 Hz, H-3); 3.02-2.98 (m, 2H, H-4 H-5); 2.95 (td, 1H, J=8.6; 4.1 Hz, H-2); 2.80-2.70 (m, 1H, —HN—CH$_2$—); 2.52-2.44 (m, 1H, —HN—CH$_2$—); 2.14 (bs; 1H, NH); 1.42-1.32 (m, 2H, +—NH—), 1.29-1.17 (m, 18H, —CH$_2$—CH$_2$—); 0.85 (t, 3H, J=6.5 Hz, —CH$_3$—CH$_2$—).

$^{13}$C NMR (DMSO-d$_6$): δ 90.8 (C-1), 77.6 (C-3), 77.4 (C-5), 73.5 (C-2), 70.6 (C-4), 61.4 (C-6), 45.5 (—HN—CH$_2$—), 31.3, 30.0, 29.0, 28.7, 26.8, 22.1 (—CH$_2$—CH$_2$—), 13.9 —CH$_3$—CH$_2$—).

High-resolution mass spectrometry HRMS [M+H]$^+$ calculated for C$_{18}$H$_{37}$NO$_5$: m/z 348.2750 found m/z 348.2758.

EXAMPLE 11: PREPARATION OF A COMPOUND Ik OF FORMULA

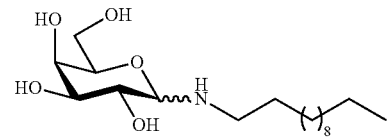

Dodecylamine (1.13 g; 6.2 mmol) is mixed with 1 g of silica (SiO$_2$). The reagents are then mixed and ground in a mortar using a pestle for 2 minutes. 1 g of galactose (5.5 mmol) is added to the mortar. The mixture is ground with the pestle for a further 2 minutes, then placed in a stainless steel jar equipped with 4 stainless steel balls which are 13 mm in diameter. The jar is placed in a Spex 8000M vibrational ball mill and agitated for 1 h 30.

The reaction crude is dissolved at reflux in 100 ml of ethanol and then filtered on a sinter comprising 50 g of silica and washed with 50 ml of hot ethanol. After evaporation of the ethanol under reduced pressure, a white solid is obtained.

Washing with 10 ml of diethyl ether at 40° C. makes it possible to obtain 1.70 g (89%) of the compound Ik in the form of a white powder.

The $^1$H and $^{13}$C NMR spectra of the compound Ik are in accordance with those described in the literature (Neto et al., J. Agric. Food Chem., 2012, 60, 10516-10522).

Mixture of α,β isomers: the ratio was not accurately determined, but the β isomer is predominant.

β isomer: $^1$H NMR (CD$_3$OD): δ 3.85 (dd, 1H, J=9.7, 3.6 Hz, H-4); 3.78 (d, 1H, J=8.4 Hz, H-1); 3.73-3.65 (m, H-6a, H-6b); 3.49-3.31 (m, 3H, H2, H-3, H-5), 2.97-2.79 (m, 1H, —HN—CH$_2$—); 2.68-2.52 (m, 1H, —HN—CH$_2$—), 1.58-1.41 (m, 2H, —CH$_2$—CH$_2$—NH—); 1.39-1.17 (m, 18H, —CH$_2$—CH$_2$—); 0.90 (t, 3H, J=6.6 Hz, —CH$_3$CH$_2$—).

$^{13}$C NMR (CD$_3$OD): δ92.5 (C-1), 77.5-75.8 (2s, C-3, C-5), 72.5 (C-2), 70.7 (C-4), 62.7 (C-6), 47.2 (—HN—CH$_2$—), 33.1, 31.2, 30.8, 30.5, 28.4, 23.7 (—CH$_2$—CH$_2$—), 14.4 —CH$_3$—CH$_2$—).

High-resolution mass spectrometry HRMS [M+H]$^+$ calculated for C$_{18}$H$_{37}$NO$_5$: m/z 348.2750 found m/z 348.2757.

EXAMPLE 12: PREPARATION OF A COMPOUND Il OF FORMULA

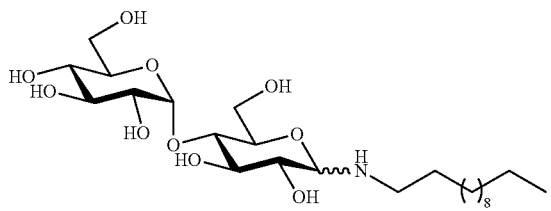

Dodecylamine (0.56 g; 3.05 mmol) is mixed with 1 g of maltose monohydrate (2.77 mmol) in a mortar using a pestle for 2 minutes, then placed in a stainless steel jar equipped with 4 stainless steel balls which are 13 mm in diameter. The jar is placed in a Spex 8000M vibrational ball mill and agitated for 3 h.

The reaction crude is dissolved at reflux in 100 ml of ethanol. After evaporation of the ethanol under reduced pressure, an off-white solid is obtained.

Washing with 20 ml of diethyl ether at 40° C. makes it possible to obtain 1.24 g (88%) of the compound Il in the form of a beige powder.

Mixture of α,β isomers: α/β: 10/90;

β isomer: $^1$H NMR (CD$_3$OD): δ5.19 (d, 1H, J=3.6 Hz, H-1'); 3.91-3.80 (m, 4H, H-1, H-6a and H-6'); 3.76-3.60 (m, 4H, H-3, H-3', H05 and H-6b); 3.58 (t, 1H, J=9.3 Hz, H-4'); 3.50 (dd, 1H, J=9.6, 3.6 Hz, H-2'); 3.39-3.36 (m, 1H, H-5'); 3.32 (t, 1H, J=9.6 Hz, H-4); 3.17 (t, 1H, J=8.7 Hz, H-2); 2.97-2.88 (m, 1H, —HN—CH$_2$—); 2.69-2.60 (m, 1H, —HN—CH$_2$—); 1.59-1.21 (m, 20H, —CH$_2$—CH$_2$CH$_2$—); 0.90 (t, 3H J=6.5 Hz, CH$_3$—CH$_2$—).

$^{13}$C NMR (CD$_3$OD): δ102.9 (C-1'), 91.8 (C-1), 81.6 (C-4'), 78.6 (C-3'), 77.5 (C-5'), 75.0 (C-3), 74.7 (C-5), 74.5 (C-2), 74.1 (C-2'), 71.5 (C-4), 62.7 (C-6), 62.2 (C-6'), 47.2 (—HN—CH$_2$—), 33.0, 31.0, 30.7, 30.4, 28.4, 23.7 (—CH$_2$—CH$_2$—), 14.4 (CH$_3$—CH$_2$—).

High-resolution mass spectrometry HRMS [M+H]$^+$ calculated for C$_{24}$H$_{47}$NO$_{10}$: m/z 510.3249 found m/z 510.3257.

EXAMPLE 13: PREPARATION OF A COMPOUND Im OF FORMULA

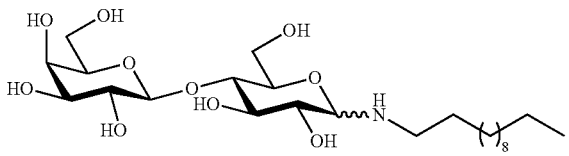

Dodecylamine (0.56 g; 3.05 mmol) is mixed with 1 g of lactose monohydrate (2.77 mmol) in a mortar using a pestle for 2 minutes, and then placed in a stainless steel jar equipped with 4 stainless steel balls which are 13 mm in diameter. The jar is placed in a Spex 8000M vibrational ball mill and agitated for 6 h.

The reaction crude is dissolved at reflux in 150 ml of ethanol, then slowly cooled to ambient temperature. The mixture is filtered on Celite®. After evaporation of the ethanol under reduced pressure, a white solid is obtained. The process is repeated twice.

Washing with 20 ml of diethyl ether at 40° C. makes it possible to obtain 0.77 g (55%) of the compound Im in the form of a white powder.

Mixture of α,β isomers: α/β: 31/69;

β isomer: $^1$H NMR (Pyr-d$_5$): δ5.19 (d, 1H, J=8.1 Hz, H-1'); 4.59-4.42 (m, 5H, H-2', H-6b and H-6'); 4.40-4.33 (m, 2H, H-1 and H-6b); 4.26-4.20 (m, 2H, H-3 and H-4'); 4.17-4.09 (m, 2H, H-3' and H-4); 3.87-3.78 (m, 1H, H-2); 3.16-3.07 (m, 1H, —HN—CH$_2$—); 2.82-2.70 (m, 1H, —HN—CH$_2$—); 1.59-1.11 (m, 20H, —CH$_2$—CH$_2$—); 0.86 (t, 3H J=6.6 Hz, CH$_3$—CH$_2$—).

$^{13}$C NMR (Pyr-d$_5$): δ105.6 (C-1'), 91.8 (C-1), 82.4 (C-4' —4'), 77.0 (2s, C-4 and C-4), 74.9 (C-3'), 74.6 (C-2), 72.2 (C-2'), 69.8 (2s, C-5 and C-5'), 62.3 (C-6'), 61.8 (C-6), 46.5 (—HN—CH$_2$—), 31.8, 30.3, 29.7, 29.4, 27.4, 22.7 (—CH$_2$—CH$_2$—), 14.0 (CH$_3$—CH$_2$—).

High-resolution mass spectrometry HRMS [M+H]$^+$ calculated for C$_{24}$H$_{47}$NO$_{10}$: m/z 510.3249 found m/z 510.3272.

EXAMPLE 14: PREPARATION OF A COMPOUND IIa OF FORMULA

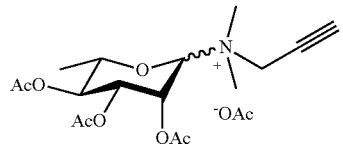

Iodomethane (0.88 g; 6.2 mmol) is mixed with 1.5 g of silica (SiO$_2$). 0.5 g (2.4 mmol) of the compound Ia (example 1) is then added to this mixture, then placed in a stainless steel jar equipped with 4 stainless steel balls which are 13 mm in diameter. The jar is placed in a Spex 8000M vibrational ball mill and agitated for 5 h.

The reaction crude is dissolved in 50 ml of ethanol, then filtered on a sinter comprising 50 g of silica and washed with 50 ml of hot ethanol. After evaporation of the ethanol under reduced pressure, a yellow oil is obtained.

The crude product obtained is then dissolved in 5 ml of acetic anhydride and 0.03 g of cerium trifluoromethanesulfonate (triflate) is added. The mixture is stirred at 50° C. for 2 h. The solution is dried under reduced pressure, then diluted with 30 ml of water. The by-products formed are then extracted 3 times with 30 ml of ethyl acetate. The aqueous phase is dried by lyophilization. The product obtained is purified by silica gel column chromatography (with a dichloromethane/methanol mixture: 8/2) to obtain 0.43 g (49%) of a compound IIa which is in the form of a yellow oil.

Mixture of α,β isomers: the ratio was not accurately determined, however the α isomer is predominant.

β isomer: $^1$H NMR (D$_2$O): δ5.28 (m, 1H, H-3); 5.21 (t, 1H, J=2.3 Hz, H-4); 5.10 (d, 1H, J=0.8 Hz, H-1); 4.88 (dd, 1H, J=2.7, 0.8 Hz, H-2); 4.65-4.36 (dd, 2H, J=5.8, 2.4 Hz, —N—CH$_2$—); 4.13-4.02 (m, 1H, H-5); 3.42 (s, 3H, —N(CH$_3$)$_2$); 3.40 (m, 4H, —N(CH$_3$)$_2$ and HC≡C—); 3.06 (s, 3H, CH$_3$CO—); 2.22-2.19 (3s, 9H, CH$_3$CO—); 1.42 (d, 3H, J=6.2 Hz, H-6).

$^{13}$C NMR (D$_2$O): δ172.6, 172.1, 172.0 (CO); 90.8 (C-1); 73.6 (C-5), 72.5 (C-3), 69.9 (C-3 and HC≡C), 64.8 (C-2), 53.7 (—N—CH$_2$—), 48.4, 47.7 (—N(CH$_3$)$_2$), 41.83 (CH$_3$CO—); 19.9 (CH$_3$—CO—) 16.0 (C-6).

Low-resolution mass spectrometry: m/z [M]$^+$
mass calculated=356.1704
mass measured=355.8

EXAMPLE 15: PREPARATION OF A COMPOUND IIb OF FORMULA

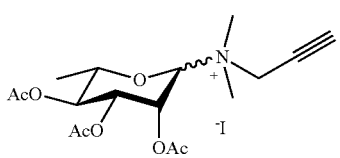

Iodomethane (0.81 g; 5.7 mmol) is mixed with 1.5 g of silica (SiO$_2$). 0.5 g (2.3 mmol) of the compound Ib (example 2) is then added to this mixture, then placed in a stainless steel jar equipped with 4 stainless steel balls which are 13 mm in diameter. The jar is placed in a Spex 8000M vibrational ball mill and agitated for 5 h.

The reaction crude is dissolved in 50 ml of ethanol, then filtered on a sinter comprising 50 g of silica and washed with 50 ml of hot ethanol. After evaporation of the ethanol under reduced pressure, a colorless oil is obtained.

The crude product obtained is then dissolved in 5 ml of acetic anhydride and 0.03 g of cerium trifluoromethanesulfonate (triflate) is added. The mixture is stirred at 50° C. for 2 h. The solution is dried under reduced pressure, then diluted with 30 ml of water. The by-products formed are then extracted 3 times with 30 ml of ethyl acetate. The aqueous phase is dried by lyophilization. The product obtained is purified by silica gel column chromatography (with a dichloromethane/methanol mixture: 8/2) to obtain 0.38 g (44%) of a compound IIb which is in the form of a pale yellow oil.

Mixture of α,δ isomers: the ratio was not accurately determined, however the α isomer is predominant.

a isomer: $^1$H NMR (D$_2$O): δ6.0 (d, 1H, J=2.8 Hz, H-1); 5.36 (dd, 1H, J=2.8, 10.80 Hz, H-2); 5.21 (t, 1H, J=10.0 Hz, H-3); 5.18 (m, 1H, H-4); 4.21-4.13 (m, 1H, H-5); 3.60-3.39 (m, 2H, —N—CH$_2$—); 3.26-3.21 (2s, 6H, —N(CH$_3$)$_2$); 2.39-2.21, 2.10 (3s, 9H CH$_3$—CO—; 1.83-1.40 (m, 4H, —CH$_2$—CH$_2$—), 1.47 (d, 3H, J=6.1 Hz, H-6), 1.06 (t, 3H, J=7.4 Hz, CH$_3$—CH$_2$).

$^{13}$C NMR (D$_2$O): δ171.8, 171.6 (CO); 90.0 (C-1); 74.2 (C-5); 71.6 (C-3); 69.9 (C-4), 66.1 (C-2), 64.8 (—N—CH$_2$—); 49.1, 47.7 (—N—(CH$_3$)$_2$); 24.0, 19.1 (—CH$_2$—CH$_2$—); 20.2, 20.0, 19.7 (CH$_3$—CO); 16.5 (C-6); 12.7 (—CH$_2$—CH$_3$).

Low-resolution mass spectrometry: m/z [M]$^+$
mass calculated=374.2173
mass measured=373.9

EXAMPLE 16: PREPARATION OF A COMPOUND IIIa OF FORMULA

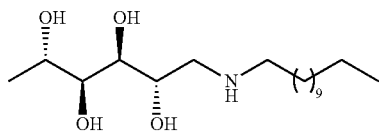

0.50 g (1.5 mmol) of compound Ie (example 5), 0.057 g (1.5 mmol) of sodium borohydride (NaBH$_4$) and 0.184 g (1.5 mmol) of benzoic acid are placed in a stainless steel jar equipped with 20 stainless steel balls (7 balls of 6 mm and 13 balls of 4 mm). The jar is placed in a Spex 8000M vibrational ball mill and agitated for 10 minutes. 0.1 ml of absolute ethanol is then added, and the jar is again placed in a ball mill and agitated for 15 minutes.

The reaction crude is dissolved in 20 ml of methanol and placed in a 100 ml round-bottomed flask equipped with a magnetic bar. 1 ml of hydrochloric acid (37%) is added and the reaction medium is stirred at ambient temperature for 1 h. A white precipitate forms, which is filtered on a sinter.

The isolated precipitate is placed in a 100 ml round-bottomed flask equipped with a magnetic bar, with 25 ml of methanol. The mixture is then treated on an Amberlite IRA 402-OH$^-$ anion exchange resin, at ambient temperature for 2 h. After filtration on a sinter, the solvent is eliminated under reduced pressure to give 0.32 g (62%) of the compound IIIa in the form of a white powder.

$^1$H NMR (Pyr-d$_5$): δ 4.72 (d, 1H, J=7.0 Hz, H-3); 4.54-4.22 (m, 2H, H-2 and H-5), 4.29 (d, 1H, J=7.4 Hz, H-4, 3.41 (qd, 2H, J=5.9, 11.6 Hz, —CH$_2$—NH—), 2.71-2.61 (m, 2H, —NH—CH$_2$—CH$_2$), 1.69 (d, 3H, J=6.1 Hz, H-6), 1.50-1.15 (m, 20H, —CH$_2$—CH$_2$—), 0.88 (t, 3H J=6.3 Hz, —CH$_2$—CH$_3$).

$^{13}$C NMR (Pyr-d$_5$): δ 75.3 (C-4), 74.1 (C-3), 70.5 (C-2), 69.4 (C-5), 54.3 (—CH$_2$—NH—), 50.1 (—HN—CH$_2$—CH$_2$), 31.8 30.2, 29.6, 29.3, 27.4, 22.7 (—CH$_2$—CH$_2$—), 21.4 (C-6), 14.0 (—CH$_2$CH$_3$).

Low-resolution mass spectrometry [M+Na]$^+$ calculated for C$_{18}$H$_{39}$NO$_4$: m/z 356.2879 found m/z 356.2.

EXAMPLE 17: PREPARATION OF A COMPOUND IIIb OF FORMULA

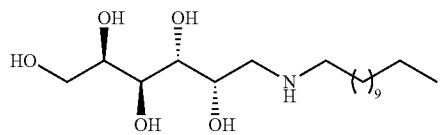

0.45 g (1.29 mmol) of compound Ij (example 10), 0.049 g (1.29 mmol) of sodium borohydride (NaBH$_4$) and 0.160 g (1.29 mmol) of benzoic acid are placed in a stainless steel jar equipped with 20 stainless steel balls (7 balls of 6 mm and 13 balls of 4 mm). The jar is placed in a Spex 8000M vibrational ball mill and agitated for 10 minutes. 0.2 ml of absolute ethanol is then added, and the jar is again placed in a ball mill and agitated for 15 minutes.

The reaction crude is dissolved in 20 ml of methanol and placed in a 100 ml round-bottomed flask equipped with a magnetic bar. 1 ml of hydrochloric acid (37%) is added and the reaction medium is stirred at ambient temperature for 1 h. A white precipitate forms, which is filtered on a sinter.

The isolated precipitate is placed in a 100 ml round-bottomed flask equipped with a magnetic bar, with 25 ml of methanol. The mixture is then treated on an Amberlite IRA 402-OH⁻ anion exchange resin, at 55° C. for 3 h. After filtration on a sinter, the solvent is eliminated under reduced pressure to give 0.186 g (41%) of the compound IIIb in the form of a white powder.

$^1$H NMR (Pyr-d$_5$): δ 4.76 (dd, 1H, J=1.0, 4.8 Hz, H-3); 4.65-4.59 (m, 1H, H-5), 4.65-4.55 (m, H, H-6a), 4.54-4.47 (m, 2H, H-2 and H-4), 4.39 (dd, 1H, J=5.7, 10.7 Hz, H-6b), 3.24 (qd, 2H, J=4.3, 11.6 Hz, —CH$_2$—NH—), 2.67-2.51 (m, 2H, —NH—CH$_2$CH$_2$), 1.50-1.15 (m, 20H, —CH$_2$—CH$_2$), 0.93 (t, 3H J=6.5 Hz, 13 CH$_2$—CH$_3$).

$^{13}$C NMR (Pyr-d$_5$): δ72.6 (C-5), 72.4 (C-2 and C-4), 72.3 (C-3), 65.4 (C-6), 51.7 (—CH$_2$—NH—), 50.0 (—HN—CH$_2$—CH$_2$), 31.8 30.0, 29.6, 29.3, 22.7 (—CH$_2$—CH$_2$—), 14.0 (—CH$_2$—CH$_3$).

Low-resolution mass spectrometry [M+Na]⁺ calculated for C$_{18}$H$_{39}$NO$_5$: m/z 372.2828 found m/z 372.2.

EXAMPLE 18: PREPARATION OF A COMPOUND IIIc OF FORMULA

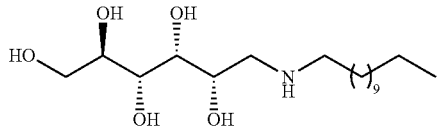

0.50 g (1.44 mmol) of compound Ik (example 11), 0.054 g (1.44 mmol) of sodium borohydride (NaBH$_4$) and 0.176 g (1.44 mmol) of benzoic acid are placed in a stainless steel jar equipped with 20 stainless steel balls (7 balls of 6 mm and 13 balls of 4 mm). The jar is placed in a Spex 8000M vibrational ball mill and agitated for 10 minutes. 0.2 ml of absolute ethanol is then added, and the jar is again placed in a ball mill and agitated for 15 minutes.

The reaction crude is dissolved in 20 ml of methanol and placed in a 100 ml round-bottomed flask equipped with a magnetic bar. 1 ml of hydrochloric acid (37%) is added and the reaction medium is stirred at ambient temperature for 1 h. A white precipitate forms, which is filtered on a sinter.

The isolated precipitate is placed in a 100 ml round-bottomed flask equipped with a magnetic bar, with 25 ml of methanol. The mixture is then treated on an Amberlite IRA 402-OH⁻ anion exchange resin, at 55° C. for 3 h. After filtration on a sinter, the solvent is eliminated under reduced pressure to give 0.201 g (40%) of the compound IIIc in the form of a white powder.

$^1$H NMR (Pyr-d$_5$): δ4.86-4.82 (m, 1H, H-5), 4.72-4.66 (m, 1H, H-2), 4.63 (dd, 1H, J=1.4, 8.5 Hz, H-3), 4.46 (dd, 1H, J=2.2, 8.5 Hz, H-4), 4.37 (d, 2H, J=5.9 Hz, H-6), 3.21 (d, 2H, J=5.5 Hz, —CH$_2$—NH—), 2.67-2.58 (m, 2H, —NH—CH$_2$—CH$_2$), 1.50-1.16 (m, 20H, —CH$_2$—CH$_2$), 0.87 (t, 3H J=6.5 Hz, —CH$_2$—CH$_3$).

$^{13}$C NMR (Pyr-d$_5$): δ 74.2 (C-4), 72.0 (C-3 and C-5), 69.8 (C-2), 65.0 (C-6), 54.3 (—CH$_2$—NH—), 50.2 (—HN— CH$_2$—CH$_2$), 31.8 30.3, 29.6, 29.3, 27.4, 22.7 (—CH$_2$— CH$_2$—), 14.0 (—CH$_2$—CH$_3$).

Low-resolution mass spectrometry [M+Na]⁺ calculated for C$_{18}$H$_{39}$NO$_5$: m/z 350.2828 found m/z 350.3.

EXAMPLE 19: PREPARATION OF A COMPOUND IIId OF FORMULA

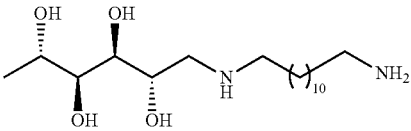

0.52 g (1.51 mmol) of compound Ii (example 9), 0.057 g (1.51 mmol) of sodium borohydride (NaBH$_4$) and 0.187 g (1.51 mmol) of benzoic acid are placed in a stainless steel jar equipped with 20 stainless steel balls (7 balls of 6 mm and 13 balls of 4 mm). The jar is placed in a Spex 8000M vibrational ball mill and agitated for 10 minutes. 0.2 ml of absolute ethanol is then added, and the jar is again placed in a ball mill and agitated for 15 minutes.

The reaction crude is dissolved in 20 ml of methanol and placed in a 50 ml round-bottomed flask equipped with a magnetic bar. 1 ml of hydrochloric acid (37%) is added and the reaction medium is stirred at ambient temperature for 1 h. A white precipitate forms, which is filtered on a sinter.

The isolated precipitate is placed in a 100 ml round-bottomed flask equipped with a magnetic bar, with 25 ml of methanol. The mixture is then treated on an Amberlite IRA 402-OH⁻ anion exchange resin, at 55° C. for 3 h. After filtration on a sinter, the solvent is eliminated under reduced pressure to give 0.22 g (42%) of the compound IIId in the form of a white powder.

$^1$H NMR (CD$_3$OD): δ3.85-3.71 (m, 3H, H-2, H-3 and H-5), 3.50 (d, 1H, J=7.8 Hz, H-4), 2.98-2.92 (m, 1H, —CH$_2$—NH—), 2.72-2.55 (m, 5H, —CH$_2$—NH—, —NH—CH$_2$—CH$_2$—, —CH$_2$—NH$_2$), 1.60-1.20 (m, 23H, —CH$_2$—CH$_2$— and H-6).

$^{13}$C NMR (CD$_3$OD): δ 75.2 (C-4), 73.5 (C-2), 70.9 (C-3), 68.7 (C-5), 53.8 (—CH$_2$—NH—), 50.6 (—HN—CH$_2$— CH$_2$), 42.5 (—CH$_2$—NH$_2$—), 33.8, 30.7, 28.4, 28.0 (—CH$_2$—CH$_2$—), 14.0 (C-6).

High-resolution mass spectrometry HRMS [M+H]⁺ calculated for C$_{18}$H$_{40}$N$_2$O$_4$: m/z 349.2988 found m/z 349.306.

Test of Biological Activity of the Compounds of Formulae (I) and (III)

I/ Antibacterial Activity

The antibacterial activity of the N-alkyl-glycosyl(di) amine derivatives of formula (I) and of the N-alkyl-glycamine derivatives of general formula (III), synthesized according to the process of the invention, was evaluated on three bacteria of different genera: *Agrobacterium tumefaciens* (Cha et al., 1998), *Pectobacterium atrosepticum* and *Dickeya dianthicola*.

*Agrobacterium tumefaciens* is an alpha-proteobacterium, and *Pectobacterium atrosepticum* and *Dickeya dianthicola* are gamma-proteobacteria. They are phytopathogenic rhizosphere bacteria. *Agrobacterium tumefaciens* is responsible for a disease called "crown gall" which results in the formation of a tumor at the infection site. Bacteria of the *Agrobacterium* genus are resistant to many antibiotics of beta-lactam type. *Pectobacterium* and *Dickeya* are the bacterial agents responsible for blackleg and soft rot in several host plants, mainly potato and also other plants such as endive, sugar beet, tomato or else carrot.

For each molecule, the minimum inhibitory concentration (MIC) and also the minimum bactericidal concentration (MBC) were evaluated.

The results presented in table 1 hereinafter correspond to the MIC values (in µg/ml) of some N-alkyl-glycosyl(di)amine derivatives of formula (I) and of some N-alkyl-glycamine derivatives of formula (III) with respect to *Agrobacterium tumefaciens*, *Pectobacterium atrosepticum* and *Dickeya dianthicola* bacteria.

TABLE 1

MIC of N-alkyl-glycosyl(di)amine derivatives of formula (I) and of N-alkyl-glycamine derivatives of formula (III) (in µg · ml$^{-1}$)

|  | Ic | Id | Ie | If | Ig | Ih | Ii | Ij | Ik | IIIa | IIIb | IIIc | IIId | 4-NPO |
|---|---|---|---|---|---|---|---|---|---|---|---|---|---|---|
| *Pectobacterium atrosepticum* | 62.5 | 62.5 | 16 | 250 | 125 | 62.5 | 8 | 16 | 16 | 32 | 32 | 62.5 | 62.5 | 125 |
| *Agrobacterium tumefaciens* | 125 | 62.5 | 4 | >500 | 125 | 62.5 | 16 | 8 | 2 | 16 | 16 | >500 | 52.5 | 125 |
| *Dickeya dianthicola* | n.d. | n.d. | 16 | n.d. | n.d. | n.d. | n.d. | n.d. | n.d. | 62.5 | 62.5 | >500 | 16 | 16 | n.d.: values not determined

The MIC is the lowest concentration of molecules (in µg/ml) which inhibits any visible culture after 36 h of culture at 30° C.

The MBC is the lowest concentration of molecules (in µg/ml) which leaves less than 0.01% of survivors of the starting inoculum after 36 h of culture at 30° C.

In order to define the MIC and the MBC of each molecule, cultures of each of two bacterial strains are set up according to the following protocol: 20 µl of a solution containing $10^6$ CFU/ml of bacterium (*Agrobacterium tumefaciens* or *Pectobacterium atrosepticum* or *Dickeya dianthicola*) are added to 10 µl of solution comprising the test molecule dissolved in DMSO or methanol, and adjusted to a final volume of 200 µl in TY medium (5 g/l tryptone and 3 g/l yeast extract). The concentration range tested for each of the molecules is between 500 and 0.5 µg/ml. The final bacterial concentration is $10^5$ CFU/well. The MIC is determined after 36 h of incubation at 30° C. by reading optical density at 600 nm. The MBC is determined by plating out 100 µl of medium from the preceding culture on a TY agar medium. The lowest concentration for which no colony grows on the dish is the MBC.

Two experiments are repeated in parallel for each sample.

4-Nitropyridine-N-oxide (4-NPO), a Sigma commercial product (CAS number: 1124-33-0), is used as reference bacteriostatic molecule with an MIC of 125 µg/ml with *Agrobacterium tumefaciens* and *Pectobacterium atrosepticum*, and of 16 µg/ml with *Dickeya dianthicola*.

An inhibition of the growth of the bacteria was observed for the compounds Ic, Id, Ie, If, Ig, Ih, Ij, Ik, IIIa, IIIb, IIIc and IIId and compared with 4-NPO which is the reference bacteriostatic molecule, after 36 h of incubation at 30° C.

The results colated in table 2 hereinafter correspond to the MBC values (in µg/ml) of N-alkyl-glycosyl(di)amine derivatives of formula (I) and of N-alkyl-glycamine derivatives of formula (III) with respect to *Agrobacterium tumefaciens*, *Pectobacterium atrosepticum* and *Dickeya dianthicola* bacteria.

TABLE 2

MBC of N-alkyl-glycosyl(di)amine derivatives of formula (I) and of N-alkyl-glycamine derivatives of formula (III) (in µg · ml$^{-1}$)

|  | Ic | Id | Ie | If | Ig | Ih | Ii | Ij | Ik | IIIa | IIIb | IIIc | IIId | 4-NPO |
|---|---|---|---|---|---|---|---|---|---|---|---|---|---|---|
| *Pectobacterium atrosepticum* | >500 | 250 | 16 | — | 250 | 125 | 16 | — | 32 | 32 | 32 | 62.5 | 62.5 | — |
| *Agrobacterium tumefaciens* | — | 250 | 8 | — | 250 | 500 | 32 | 16 | — | 62.5 | 32 | >500 | 250 | — |
| *Dickeya dianthicola* | n.d. | n.d. | 16 | n.d. | n.d. | n.d. | n.d. | n.d. | n.d. | 62.5 | 62.5 | >500 | 125 | 16 | n.d.: values not determined

The N-alkyl-glycosyl(di)amine derivatives of formula (I) and the N-alkyl-glycamine derivatives of formula (III) synthesized showed a bactericidal activity with respect to the *Agrobacterium tumefaciens*, *Pectobacterium atrosepticum* and *Dickeya dianthicola* bacteria, preferentially the compounds Id, Ie, Ig, Ih, Ii, Ij, Ik, IIIa, IIIb, IIIc and IIId.

The impact of the N-alkyl-glycosyl(di)amine derivatives of formula (I) was measured via the MICs and MBCs of the mixtures of compounds Ie/Ih, Ie/Id and Ih/Id (50/50 ratios in g/g). The same antibacterial evaluation protocol as the one described previously with the N-alkyl-glycosyl(di)amine derivatives of formula (I) was applied for these mixtures.

The following tables 3 and 4 collate the MIC and MBC results obtained after antibacterial evaluation of the mixtures of compounds Ie/Ih, Ie/Id and Ih/Id.

TABLE 3

MICs of the mixtures of compounds Ie/Ih, Ie/Id and Ih/Id (in µg/ml$^{-1}$)

|  | Ie/Ih | Ie/Id | Ih/Id |
|---|---|---|---|
| *Pectobacterium atrosepticum* | 16 | 32 | 62.5 |
| *Agrobacterium tumefaciens* | 8 | 8 | 125 |

TABLE 4

MBCs of the mixtures of compounds Ie/Ih, Ie/Id and Ih/Id (in µg/ml$^{-1}$)

|  | Ie/Ih | Ie/Id | Ih/Id |
|---|---|---|---|
| *Pectobacterium atrosepticum* | 62.5 | 62.5 | 125 |
| *Agrobacterium tumefaciens* | 62.5 | 32 | 125 |

These results show that the molecules obtained have antibacterial activities which could be exploited for protecting various plants such as potato against phytopathogenic bacteria. Moreover, the combinations of N-alkyl-glycosyl (di)amine derivatives of formula (I) also show a synergistic effect.

II/ Antifungal Activity

The antifungal activity of the N-alkyl-glycosyl(di)amine derivatives of formula (I) and of the N-alkyl-glycamine derivatives of formula (III) synthesized according to the process of the invention was evaluated on two fungi: *Fusarium roseum* and *Fusarium sambucinum*.

For this, 500 µl of solution comprising the test derivative, dissolved in DMSO or methanol, are mixed with 19.5 ml of malt agar medium (Sigma aldrich) allowing the growth of these two *Fusarium* isolates. The test derivative is prepared in 2 ml of methanol, then mixed with 18 ml of malt agar medium (Sigma aldrich). A spot of 10 µl of culture of each *Fusarium* is then deposited at the center of each Petri dish. After 10 days of incubation at 20° C., the growth diameters are measured.

The range of concentrations of N-alkyl-glycosyl(di)amine derivatives of formula (I) tested ranges from 0.1 to 25 µmol/ml.

The *Fusarium* growth on media containing the various molecules is compared with that obtained only with DMSO or methanol.

The first tests were carried out with the compound Ij at concentrations ranging from 1 to 25 µmol/ml. 500 µl of a solution comprising the compound Ij in DMSO are mixed with 19.5 ml of agar malt medium (Sigma aldrich). The results obtained are expressed as percentage inhibition of mycelial growth and are collated in table 5.

TABLE 5

Inhibition of the growth of the fungi *Fusarium roseum* and *Fusarium sambucinum* in the presence of compound Ij at various concentrations (1 to 25 µmol/ml) (as %)

|  | 1 | 2.5 | 5 | 10 | 20 | 25 |
|---|---|---|---|---|---|---|
| *Fusarium roseum* | 100 | 100 | 100 | 100 | 100 | 100 |
| *Fusarium sambucinum* | 50 | 50 | 100 | 100 | 100 | 100 |

The same antifungal evaluation protocol as the one previously described with the compound Ij was applied for other N-alkyl-glycosyl(di)amine derivatives of formula (I) and N-alkyl-glycamine derivatives of formula (III) at concentrations ranging from 1 to 20 µmol/ml. The results obtained are collated in tables 6 and 7.

2 ml of solution comprising the test compound dissolved in methanol are mixed with 18 ml of agar malt medium (Sigma aldrich) allowing the growth of these two *Fusarium* isolates. A spot of 10 µl of culture of each *Fusarium* is then deposited at the center of each Petri dish. After more than 10 days of incubation at 20° C., the growth diameters are measured. The inhibition percentages are then determined after comparison with the mycelial growth observed with the negative control (with methanol and without active compound).

TABLE 6

Inhibition of the growth of the *Fusarium roseum* fungi in the presence of N-alkyl-glycosyl(di)amine derivatives of formula (I) and of N-alkyl-glycamine derivatives of formula (III) at various concentrations (1 to 20 µmol/ml)

|  | 1 | 2.5 | 5 | 10 | 20 |
|---|---|---|---|---|---|
| Ib | 0 | 0 | 0 | 70 | 88 |
| Ic | 0 | 18 | 99 | 99 | 100 |
| Ie | 94 | 96 | 100 | 100 | 100 |
| Ih | 0 | 28 | 90 | 93 | 93 |
| Ii | 0 | 34 | 93 | 93 | 100 |
| Ik | 96 | 96 | 96 | n.d. | n.d. |
| IIIa | 100 | 100 | 100 | n.d. | n.d. |
| IIIb | 100 | 100 | 100 | n.d. | n.d. |
| IIIc | 100 | 100 | 100 | n.d. | n.d. | n.d.: values not determined

TABLE 7

Inhibition of the growth of the *Fusarium sambucinum* fungi in the presence of N-alkyl-glycosyl(di)amine derivatives of formula (I) and of N-alkyl-glycamine derivatives of formula (III) at various concentrations (1 to 20 µmol/ml)

|  | 1 | 2.5 | 5 | 10 | 20 |
|---|---|---|---|---|---|
| Ib | 0 | 0 | 4 | 76 | 90 |
| Ic | 10 | 33 | 89 | 90 | 100 |
| Ie | 95 | 96 | 100 | 100 | 100 |
| Ih | 12 | 27 | 100 | 100 | 100 |
| Ii | 28 | 60 | 100 | 100 | 100 |
| Ik | 96 | 96 | 96 | n.d. | n.d. |
| IIIa | 100 | 100 | 100 | n.d. | n.d. |
| IIIb | 96 | 96 | 100 | n.d. | n.d. |
| IIIc | 98 | 100 | 100 | n.d. | n.d. | n.d.: values not determined

These results show that the N-alkyl-glycosyl(di)amine derivatives of formula (I) and the N-alkyl-glycamine derivatives of formula (III) have a strong inhibitory activity against *Fusarium roseum* and *Fusarium sambucinum*.

Some N-alkyl-glycosyl(di)amine derivatives of formula (I) and N-alkyl-glycamine derivatives of formula (III) were also the subject of biological tests against *Phytophthora infestans* in order to determine their antifungal activity against this oomycete responsible for mildew in plants such as potato. Tests consisting in measuring their inhibitory effect in vitro were carried out.

In this approach, the inhibition diameters are determined according to the following protocol: 20 mg of N-alkyl-glycosyl(di)amine derivative of formula (I) or of N-alkyl-glycamine derivative of formula (III) are mixed with 200 µl of distilled water, until a viscous mixture is obtained. Four spots of 10 µl of this mixture are deposited at the four extremities of Petri dishes having a V8 agar medium, then a square of agar containing *Phytophthora infestans* mycelium is deposited at the center of the dish. The negative control was carried out with distilled water (without N-alkyl-glycosyl(di)amine derivative of formula (I) or N-alkyl-glycamine derivative of formula (III)) and the positive control was carried out with Ranman Top (commercial fungicide commonly used for combating mildew). The inhibition diameters of the N-alkyl-glycosyl(di)amine derivatives of formula (I) and of the N-alkyl-glycamine derivatives of formula (III), and of the positive and negative controls, were measured after 6 days, and are collated in table 8.

TABLE 8

Inhibition diameters of the N-alkyl-glycosyl(di)amine derivatives of formula (I) and of the N-alkyl-glycamine derivatives of formula (III) with respect to *Phytophthora infestans* after 6 days

| | Average diameters of inhibition zone (mm) |
|---|---|
| Ie | 21 |
| Ij | 24 |
| Ik | 24 |
| IIIa | 24 |
| IIIb | 20 |
| IIIc | 18 |
| IIId | 0 |
| Negative control (distilled water) | 0 |
| Positive control (Ranman Top) | 35 |

The results obtained after 6 days show that the N-alkyl-glycosyl(di)amine derivatives of formula (I) and the N-alkyl-glycamine derivatives of formula (III) obtained according to the invention have good antifungal activities against the oomycete *Phytophthora infestans*.

The invention claimed is:

1. A process for the synthesis of an N-alkyl-glycosyl(di)amine derivative corresponding to general formula (I) below:

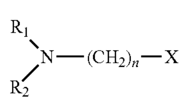

(I)

or a quaternary salt thereof, wherein $R_1$ is a glycosyl radical, $R_2$ is a hydrogen atom, a glycosyl radical, or a $C_1$-$C_{22}$ alkyl radical, n is an integer ranging from 0 to 20, X is a halogen atom, an alkyl, alkenyl or alkynyl radical, a hydroxyl group, a carboxyl or carbaldehyde group, an aryl or heteroaryl group, or an —$NR_3R_4$ group, in which $R_3$ is a hydrogen atom or a glycosyl radical, and $R_4$ is a hydrogen atom or a $C_1$-$C_{12}$ alkyl radical, with the proviso that n is different from 0 when X is an —$NR_3R_4$ group, said process consisting of the following steps:

(i) mixing an ose or oside compound and an amine of formula $R_2NH—(CH_2)_n—X$ and optionally an auxiliary in a reactor to provide a mixture, (ii) milling said mixture in a ball mill, and (iii) purifying and/or filtering the N-alkyl-glycosyl(di)amine derivative of formula (I), wherein steps (i) and (ii) are carried out without solvent.

2. The process as claimed in claim 1, wherein the ose or oside compound is a mono-, oligo- or polysaccharide comprising from 1 to 20 monosaccharide units.

3. The process as claimed in claim 1, wherein the ose or oside compound is a mono-, oligo- or polysaccharide of which the saccharide unit is chosen from threose, erythrose, deoxyribose, ribose, xylose, rhamnose, fucose, glycerose, arabinose, lyxose, allose, altrose, gulose, idose, talose, glucose, mannose, glucosamine, galactosamine, maltose, lactose or galactose.

4. The process as claimed in claim 3, wherein the saccharide unit is rhamnose, glucose, maltose, lactose or galactose.

5. The process as claimed in claim 1, wherein the mole ratio of the ose or oside compound to the amine is between 1/1 and 1/1.2.

6. The process as claimed in claim 1, wherein the balls of the mill and the mixture of the ose or oside compound and the amine of formula $R_2NH—(CH_2)_n—X$ occupy at least ⅓ of the reactor volume.

7. The process as claimed in claim 1, wherein the reactor and/or the balls of the mill are made of stainless steel, of tungsten carbide or of zirconia.

8. The process as claimed in claim 1, wherein the reactor and the balls of the mill are made of the same material.

9. The process as claimed in claim 1, wherein the milling step (ii) lasts at least 1 hour.

10. The process as claimed in claim 1, wherein the mill operates at a frequency of between 20 and 50 Hz.

11. The process as claimed in claim 1, wherein:

the quaternary salt of formula (I) has the formula (II)

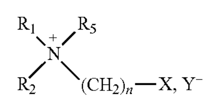

(II)

wherein $R_5$ is a hydrogen atom or a $C_1$-$C_{22}$ alkyl radical, and

Y is a halogen atom, a sulfate group $R_6O—SO_2—O—$ or a sulfonate group $R_6—SO_2—O$, in which $R_6$ is a $C_1$-$C_{12}$ alkyl radical.

12. The process as claimed in claim 4 wherein the saccharide unit is chosen from rhamnose, glucose, or galactose.

13. The process as claimed in claim 9 wherein the milling step (ii) lasts from 1 to 4 hours.

14. The process as claimed in claim 10 wherein the mill operates at a frequency of 50 Hz.

15. The process as claimed in claim 1, wherein the mixture comprises an auxiliary.

16. The process as claimed in claim 15, wherein the auxiliary is chosen from silica ($SiO_2$), alumina ($Al_2O_3$), clays or carbonates.

* * * * *